United States Patent [19]

Morin, III et al.

[11] 4,359,907
[45] Nov. 23, 1982

[54] PROCESS MONITORING APPARATUS AND METHOD

[76] Inventors: William J. Morin, III, 3202 Knudsen Ave.; Thomas E. Woodford, P.O. Box 3435, both of, Farmington, N. Mex. 87401

[21] Appl. No.: 186,974

[22] Filed: Sep. 15, 1980

[51] Int. Cl.³ .............................................. G01N 1/12
[52] U.S. Cl. ............................... 73/863.21; 73/864.81; 324/438
[58] Field of Search ............... 73/863, 863.21, 863.41, 73/863.51, 863.61, 864.81, 864.91, 349; 324/438; 55/270; 204/195 R

[56] References Cited

U.S. PATENT DOCUMENTS

| | | | |
|---|---|---|---|
| 2,082,299 | 6/1937 | Nonhebel et al. | 73/864.81 |
| 2,768,135 | 10/1956 | Adelson | 73/863.61 |
| 3,188,565 | 6/1965 | Kolb | 73/863.61 |
| 3,616,272 | 10/1971 | Goerg et al. | 204/195 |
| 4,285,792 | 8/1981 | McGandy | 204/195 |

*Primary Examiner*—S. Clement Swisher
*Attorney, Agent, or Firm*—Gregory J. Nelson

[57] ABSTRACT

A method and apparatus for the continuous monitoring of process stream chemical process. The apparatus includes a canister or reservoir with a sampling chamber having an inlet for the process stream in an upper portion of the canister and an outlet returning the sample to the process vessel. The inlet and outlet are offset from one another and sized to maintain a positive pressure within the sampling chamber so that a turbulent flow pattern through the sampling chamber is established. A measuring device such as an electrode assembly depends into the chamber within the canister and transmits a representative signal to a remote analytical instrument. Entrained gases are removed from the upper portion of the chamber via conduit and valve.

8 Claims, 3 Drawing Figures

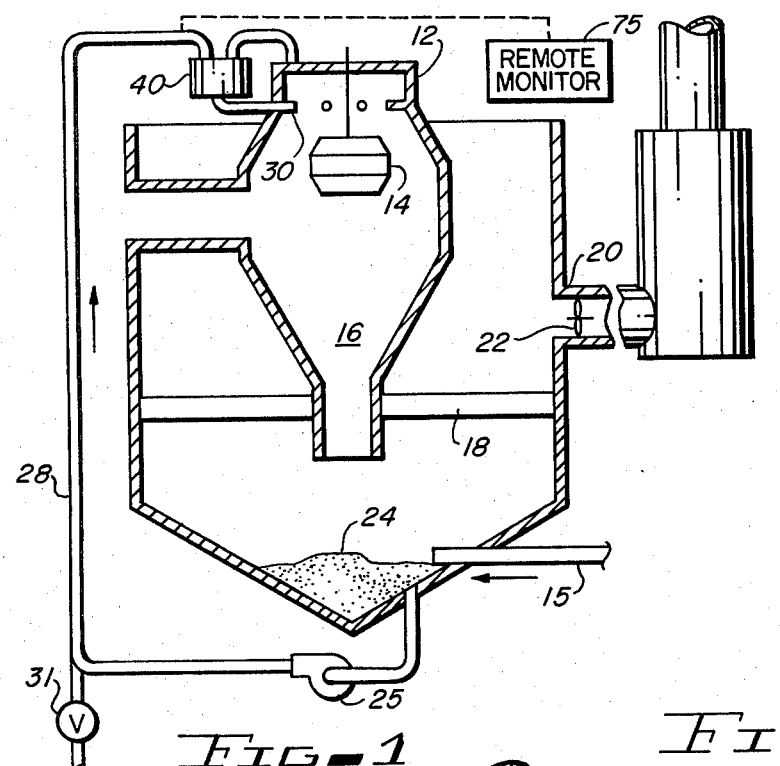
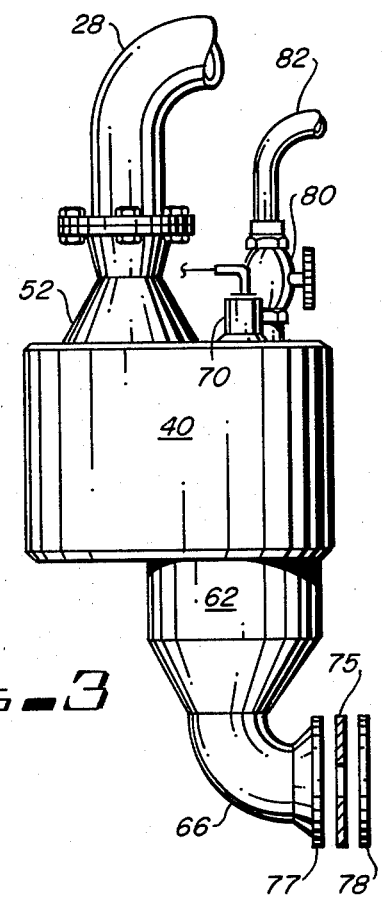
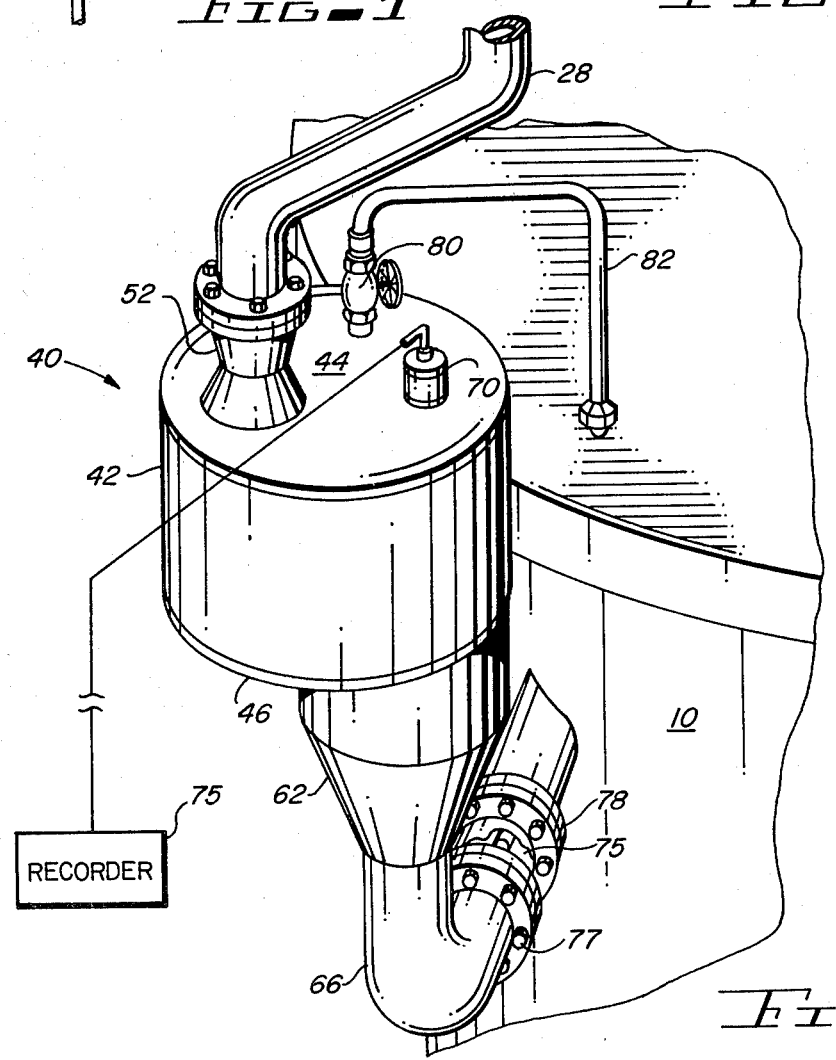
Fig-1
Fig-3
Fig-2

PROCESS MONITORING APPARATUS AND METHOD

The present invention relates generally to a method and apparatus for automatically sampling and analyzing process streams.

More particularly, the present invention is directed to a process and a related apparatus and instrumentation for continuously sampling and monitoring the pH of a process stream in a wet scrubber.

The combustion of various fossil fuels, such as oil and coal, produce products of combustion which include constituents including sulphur dioxide and flyash. Sulphur dioxide poses particularly serious problems and stringent regulations of $SO_2$ emissions have been imposed by various regulatory agencies. Utility and power generating companies, which are substantial users of fossil fuels, are subject to such regulation and therefore must employ methods of purifying resulting combustion gases to reduce emission of sulphur dioxide particulate material.

A number of systems have been developed for treating combustion gases to at least partially remove sulphur dioxide and other objectionable constituents from the gases. One method of treating stack gases to remove objectionable contaminates is to subject the stack gas to wet scrubbing to affect absorption of the sulphur dioxide and water. In order to improve the effectiveness of such scrubbing systems, acqueous slurries of lime-containing materials such as calcium carbonate, dolomite, quick-lime and the like are often added. The reactants such as high calcium lime or magnesium lime is directly injected into the scrubber to maintain the scrubber slurry at a pH of approximately 6.2 to 7.5 and the proper pH must be maintained to prevent scaling and deposition of lime on equipment surfaces.

In order to control the addition of reactants, it is customary practice to monitor pH by diverting a slip stream of reagent containing slurry from an appropriate location such as from a recycle pump discharge header. The slip stream is diverted to a sampling location remote from the process vessel. The transmission conduits for the sample are susceptible to plugging and in some areas must be insulated in order to prevent freezing. Additionally, the monitoring instruments are often mounted in an atmosphere that is very humid causing problems with the instruments and related electrical wiring and connections. Further, the sample stream in such installations also represent a small volume of the total process flow and may not provide a representative sample, therefore, yielding inaccurate pH or other process parameter indications. Accordingly, there exists a need for an improved process monitoring method and apparatus.

Briefly, according to the present invention, a method and apparatus for the continuous sampling of a process stream and monitoring a process parameter is provided. The method and apparatus involves diverting a representative sample stream from the process vessel to an adjacently located sampling reservoir. The inlet and outlet of the sampling reservoir are located and sized so that a turbulent fluid motion is induced within the reservoir and a positive pressure maintained therein. The outlet from the reservoir is directed back to the process vessel. The process parameter is measured by an appropriate device such as pH measuring electrode depending into the reservoir. The measuring apparatus is connected to an appropriate analytical instrument such as a monitor or recorder at a remote location. A vent line is connected to an upper portion of the reservoir and entrained gases are directed to the process vessel.

The above and other objects and advantages of the present invention will be more readily appreciated and understood from the following description, claims and drawings in which:

FIG. 1 is a sectional view through a wet scrubber illustrating the present invention with certain components being shown schematically for purposes of representation;

FIG. 2 is a perspective view of a portion of a wet scrubber showing the sampling reservoir connected thereto; and FIG. 3 is a side view of the monitoring instrument of the present invention.

Turning now to the drawings, FIG. 1 represents a typical application of the sampling method and apparatus of the present invention. In the following description, the present invention and method will be described in connection with a wet scrubber, however, it will be understood the present method and apparatus has application to a wide range of process applications and may be used to monitor the various parameters such as pH, temperature, oxidation-reduction potential, flow rate and the like.

A boiler produces a gas stream from combustion of fossil fuels such as coal and the gaseous products of combustion are introduced into wet scrubber 10 at central stack 12. The products of combustion vary somewhat with the type of fuel which may be coal, oil or the like. Generally, the products of combustion resulting from the complete combustion of fossil fuels are $CO_2$, $H_2O$ and, if sulphur is present as it is in many fuels, $SO_2$. Accompanying these components are nitrogen and oxygen.

The scrubber 10 can be of any vertical or horizontal type. For purposes of illustration, the scrubber illustrated is generally of the type of vertical scrubber manufactured by Chemical Construction Company which includes a centrally located conical baffle 14 sometimes termed a "plumb bob" located adjacent central venturi section 16. The baffle 14 is adjustable to control pressure drop across the venturi. The incoming gas stream is directed down the apex of the baffle in a washing zone.

The reactant, such as high calcium lime or magnesium lime, is introduced via line 15 into the washing zone of the scrubber 12 at a location below the conical flow diversion baffle at the discharge of the venturi section. A generally horizontal mist separator 18 is positioned within the scrubber to separate the entrained moisture from the scrub gas phase. Scrub gas is removed by a conduit 20 above the mist separator under the influence of an induction fan 22 into entrainment units, not shown.

A separate aqueous slurry phase 24 collects in the lower conical portion 21 of the scrubber. Slurry is recycled by a pump 25 through line 28 to tangential injection nozzles 30. Sulphur dioxide in the combustion gases is chemically absorbed and remains in the slurry as calcium sulfite and calcium sulfate. A controlled quantity of slurry is discharged across valve 31 to a remote thickener to maintain the desired solids concentration. In order to prevent excessive deposition of lime on vessel and piping surfaces, the pH within the scrubber should be maintained at about near-neutral condition as, for example, a pH range of 6.5 to 7.5. The reactant injection unit is controlled from analyzing or monitoring pH within the unit.

FIG. 2 illustrates the present invention as applied to the scrubber 10. The continuous monitoring or sampling unit of the present invention includes a sampling reservoir 40. Sampling reservoir 40 is shown as having generally cylindrical side wall 42 and having top and bottom walls 44 and 46 respectively defining sampling chamber 50. Discharge line 28 extends into the top of the scrubber vessel 10 as a conduit for the fluid stream to be sampled. For example, in a wet scrubber of the type discussed above, conduit 28 withdraws a lime-containing slurry that is recycled to the tangent nozzles 30. Line 28 connects to inlet reducer 52 which discharges into chamber 56 through top plate 44. Reducer 52 is shown as convergent-divergent which provides a venturi effect increasing the flow velocity through the reducer. Reducer 52 is positioned in a non-concentric position with respect to top plate 44.

The sample stream introduced into a reservoir chamber 56 is returned to the scrubber 10 via return conduit 64 which includes elbow 66 connected to outlet reducer 62. Outlet 62 is laterally offset from the axial center line of inlet 52. With the inlet 52 and outlet 62 being offset, a turbulent flow pattern is induced within chamber 56. The turbulent flow pattern through chamber 50 from the inlet to the outlet causes the interior walls of the chamber to be continually "scrubbed" preventing deposition and accumulation or build-up of lime or other materials on the chamber surfaces. As orifice 75 having a diameter less than the diameter of inlet 52 is interposed between flanges 77 and 78 in line 64 imposing a restriction in the outlet to maintain a positive pressure within chamber 50.

The appropriate process parameter is measured by sensing device 70 as for example one or more electrode assemblies depending into chamber 50 and positioned on upper plate 44. In the case of pH measurement, the appropriate sensing device can be a multipurpose electrode and transmitter unit such as the type manufactured by Leeds & Northrup or by The Beckman Company. The unit includes a transmitter which is environmentally sealed or encapsulated. The measuring and reference electrodes and optional automatic temperature compensator are directly connected to a preamplifier. The preamplifier conditions and amplifies the electrode signal and the signal can then be transmitted by an appropriate wire to a remote receiver 75. The remote receiver 75 is an analytical instrument which may monitor and/or record the measured parameter. As pointed out above, the measured parameter may be pH, redox (ORP), temperature of flow rates, or any other desired process parameter.

Adjustable valve 80 communicates with chamber 50 at top 44. Valve 80 has its discharge connected via conduit 82 to the top of scrubber 10. Entrained gases which may collect in the upper part of chamber 50 may be bled-off and returned to the scrubber vessel 12 across valve 80.

In order to test the effectiveness of the sampling apparatus and method of the present invention, a unit as shown and described above was constructed and was attached to a vertical scrubber of the type described above. The vertical scrubber inlet was connected to treat combustion gases from a 170 megawatt coal fired unit at the Four Corners Power Plant near Farmington, New Mexico. The reservoir constructed had an overall height of approximately one foot, ten inches and a diameter of approximately two feet. Outlet reducer 62 had a major diameter of twelve inches. The inlet 54 had a major diameter of six inches at top wall 44 with the inlet line 28 having a diameter of four inches. Line 28 was connected to one of six tangent nozzle feed lines exiting from the scrubber 12 at 11,000 GPM through pump 24. An electrode assembly as described above for measuring pH was placed in the top 44 of the reservoir and connected to a remote monitoring and recording instrument 75. Bleed valve 80 was provided to discharge any gases that might accumulate in the upper part of the chamber 56. Orifice 75 was selected to maintain a positive pressure of approximately 4 to 6 psi within chamber 56. The pressure within the scrubber 10 at the outlet of nozzles 30 was approximately 12" negative.

The unit was placed in operation and operated for approximately two months on a continuous basis. During regular intervals, the unit was inspected and it was found the interior surface of the reservoir was free of any substantial build-up or scaling. The continuous vent line 82 eliminated any entrained gases and assured that the reservoir 56 would stay full at all times and, accordingly, more representative samples were obtained. With the present system, a large volume of scrubber slurry is sampled and a much better representative sample is obtained which is believed to give a more accurate pH reading. Another important advantage noted was that the sampling unit was located at the scrubber with the instrumentation such as an analytical instrument 75 being remotely located. Thus, the instrument 75 operates in an improved environment. Since the sampling chamber was entirely self-contained and was a closed system, overflowing of this sampling chamber causing maintenance problems does not occur.

The exact flow pattern within the chamber 56 was not precisely determined but is believed to be extremely turbulent due to the relationship of the inlet and outlet and velocities encountered. No appreciable scaling or plugging was noted. The probes 70, after several months of operation remained substantially scale-free and intact and within calibration limits. In contrast, the previous sampling system in which slurry was drained-off to a sampling bucket, the probes were either broken or scaled within only 2 or 3 days of operation. Another important advantage noted as a result of the test, was reduced cost of installation and maintenance.

As pointed out above, the monitoring system of the present invention was described as specifically applied to a wet scrubber, it is not limited thereto. The present invention can be employed in any process where a sample stream may be diverted and monitored for a particular process parameter.

It will be obvious to those skilled in the art to make various changes, modifications and alterations to the invention described herein. To the extent that these changes, alterations and modifications do not depart from the spirit and scope of the appended claims, they are intended to be encompassed therein.

We claim:

1. An apparatus for the continuous monitoring of a process parameter in a process having a process vessel, said apparatus comprising:
   (a) a closed reservoir defining a sampling chamber having an inlet communicating with an upper portion of the chamber and a single outlet communicating with a lower portion of said chamber, said inlet and outlet being oppositely disposed and transversely offset whereby a turbulent flow pattern is established within said chamber;
(b) first conduit means connecting said process vessel to said inlet;
(c) second conduit means connecting said outlet to said vessel for returning a sample stream to the vessel, said second conduit means including flow restriction means therein whereby a positive pressure is established in said chamber; and
(d) sensing means depending into said sampling chamber for transmitting a signal indicative of said process parameter to a remote analytical instrument.

2. The reservoir of claim 1 further including vent means connected to said sampling chamber for returning entrained gases to said process vessel.

3. The apparatus of claim 2 wherein said reservoir is cylindrical and wherein said outlet has a diameter substantially greater than said inlet.

4. The apparatus of claim 3 wherein said process vessel comprises a wet scrubber and said parameter being measured is pH.

5. The method for the continuous monitoring of a process parameter in a process having a process vessel, said method comprising:

(a) establishing a sampling chamber having an inlet and an upper portion and an outlet in a lower portion with said inlet and outlet being oppositely disposed and transversely offset from one another;
(b) introducing a representative process sample into said sampling chamber at said inlet;
(c) establishing a turbulent flow pattern from said inlet to said outlet;
(d) restricting the discharge flow thereby maintaining a positive pressure in said chamber greater than the pressure in said vessel;
(e) returning said process sample to said process vessel; and
(f) continually monitoring said process sample in said chamber to obtain a reading indicative of said parameter.

6. The process of claim 5 further including the step of removing entrained gases at an upper portion of said chamber and returning said gases to said process vessel.

7. The method of claim 6 wherein said measurement is transmitted to an analytical instrument remote from said chamber.

8. The method of claim 7 wherein said process vessel is a wet scrubber and wherein the process parameter measured is pH.

* * * * *

UNITED STATES PATENT AND TRADEMARK OFFICE
CERTIFICATE OF CORRECTION

PATENT NO. : 4,359,907
DATED : November 23, 1982
INVENTOR(S) : William J. Morin, III and Thomas E. Woodford It is certified that error appears in the above-identified patent and that said Letters Patent are hereby corrected as shown below:

```
Column 2, line 42, change "Chemical" to --Chemico--.
Column 3, line 15, change "56" to --50--.
Column 3, line 21, change "56" to --50--.
Column 3, line 25, change "56" to --50--.
Column 4, line 2, change "54" to --52--.
Column 4, line 12, change "56" to --50--.
Column 4, line 14, change "56" to --50--.
Column 4, line 22, change "56" to --50--.
Column 4, line 35, change "56" to --50--.
```

In Drawing Figure 2, numeral "64" should be included to indicate the return conduit.

In Drawing Figure 2, numeral "50" should be included to indicate the sampling chamber.

Signed and Sealed this

Twelfth Day of April 1983

[SEAL]

Attest:

GERALD J. MOSSINGHOFF

Attesting Officer    Commissioner of Patents and Trademarks